United States Patent
Sato et al.

(10) Patent No.: US 10,010,917 B2
(45) Date of Patent: Jul. 3, 2018

(54) PLASTIC WORKING METHOD OF METALS AND PLASTIC WORKING APPARATUS

(75) Inventors: Koichi Sato, Tokyo (JP); Masahiro Kubo, Tokyo (JP); Masaaki Mizumura, Tokyo (JP); Tohru Yoshida, Tokyo (JP)

(73) Assignee: NIPPON STEEL & SUMITOMO METAL CORPORATION, Tokyo (JP)

(*) Notice: Subject to any disclaimer, the term of this patent is extended or adjusted under 35 U.S.C. 154(b) by 760 days.

(21) Appl. No.: 14/400,753

(22) PCT Filed: May 17, 2012

(86) PCT No.: PCT/JP2012/062691
§ 371 (c)(1),
(2), (4) Date: Nov. 12, 2014

(87) PCT Pub. No.: WO2013/171884
PCT Pub. Date: Nov. 21, 2013

(65) Prior Publication Data
US 2015/0143861 A1    May 28, 2015

(51) Int. Cl.
*B21D 22/10*    (2006.01)
*B21C 37/00*    (2006.01)
(Continued)

(52) U.S. Cl.
CPC ............. *B21C 37/00* (2013.01); *B21C 51/00* (2013.01); *B21D 22/022* (2013.01);
(Continued)

(58) Field of Classification Search
CPC .. B21D 26/033; B21D 26/055; B21D 26/021; B21D 22/022; B21D 22/208;
(Continued)

(56) References Cited

U.S. PATENT DOCUMENTS 4,352,280 A * 10/1982 Ghosh ................. B21D 26/021
72/364
4,901,552 A * 2/1990 Ginty ................... B21D 26/055
29/421.1
(Continued)

FOREIGN PATENT DOCUMENTS

CN    102397942 A    4/2012
DE    102006015793    6/2007
(Continued)

OTHER PUBLICATIONS

Office Action dated Jun. 26, 2015 issued in corresponding Chinese Application No. 201280073152.3.
(Continued)

*Primary Examiner* — David B Jones
(74) *Attorney, Agent, or Firm* — Birch, Stewart, Kolasch & Birch, LLP

(57) ABSTRACT

Provided is a plastic working method of steel including austenite, the method including: analyzing a strain ratio βx of an estimated breaking point which is specified during plastic deformation of the steel; heating a steel such that a local temperature $T_{local}$ is within a temperature range indicated by the following expression 1, when $T_{\beta x}$ represents a strain-induced-transformation-maximum-ductility-temperature in the unit of °C. for the strain ratio βx, $\sigma L_{\beta x}$ represents the standard deviation of a fitted curve of critical equivalent strain which depends on the strain ratio βx on a lower temperature side than $T_{\beta x}$, $\sigma H_{\beta x}$ represents the standard deviation of a fitted curve of critical equivalent strain which depends on the strain ratio βx on a higher temperature side than $T_{\beta x}$, and $T_{local}$ represents a local temperature in the unit of °C. of the estimated breaking point; and plastically deforming the steel after heating:

$$T_{\beta x} - 2 \times \sigma L_{\beta x} \leq T_{local} \leq T_{\beta x} + 1.25 \times \sigma H_{\beta x} \quad \text{(Expression 1)}.$$

11 Claims, 6 Drawing Sheets

(51) Int. Cl.
| | |
|---|---|
| B21D 22/20 | (2006.01) |
| B21D 26/021 | (2011.01) |
| C21D 1/78 | (2006.01) |
| C21D 7/02 | (2006.01) |
| C21D 7/13 | (2006.01) |
| C21D 8/00 | (2006.01) |
| C21D 9/46 | (2006.01) |
| C21D 11/00 | (2006.01) |
| G01N 3/18 | (2006.01) |
| B21C 51/00 | (2006.01) |
| B21D 22/02 | (2006.01) |
| B21D 37/16 | (2006.01) |

(52) U.S. Cl.
CPC ......... *B21D 22/208* (2013.01); *B21D 26/021* (2013.01); *B21D 37/16* (2013.01); *C21D 1/78* (2013.01); *C21D 7/02* (2013.01); *C21D 7/13* (2013.01); *C21D 8/005* (2013.01); *C21D 9/46* (2013.01); *C21D 11/00* (2013.01); *G01N 3/18* (2013.01); *G01N 2203/0017* (2013.01); *G01N 2203/0092* (2013.01); *G01N 2203/0226* (2013.01)

(58) Field of Classification Search
CPC ......... B21D 37/16; B21C 37/00; B21C 51/00; C21D 1/78; C21D 7/02; C21D 7/13; C21D 8/005; C21D 9/46; C21D 11/00; G01N 3/18
USPC ........................................................... 72/61
See application file for complete search history.

(56) References Cited

U.S. PATENT DOCUMENTS

| | | | | |
|---|---|---|---|---|
| 5,214,949 A | * | 6/1993 | Cadwell | B21D 26/055 72/342.94 |
| 6,550,302 B1 | | 4/2003 | Gosh | |
| 7,024,897 B2 | * | 4/2006 | Pfaffmann | B21D 26/033 148/520 |
| 2009/0025445 A1 | | 1/2009 | Amborn | |
| 2009/0288466 A1 | | 11/2009 | Tang et al. | |

FOREIGN PATENT DOCUMENTS

| | | |
|---|---|---|
| EP | 1688196 | 8/2006 |
| EP | 1911536 | 4/2008 |
| JP | 2004-190050 | 7/2004 |
| JP | 2004-330230 | 11/2004 |
| JP | 2005-177805 | 7/2005 |
| JP | 2007-111765 | 5/2007 |
| JP | 2009-136880 | 6/2009 |
| JP | 2012-122130 | 6/2012 |
| RU | 32014086 | 7/1995 |
| RU | 2417852 | 5/2011 |
| SU | 1556792 | 4/1990 |
| TW | 289000 | 10/1996 |
| TW | 225100 | 12/2004 |
| TW | 317760 | 12/2009 |
| WO | WO 95/29268 | 11/1995 |
| WO | 02092248 | 11/2002 |
| WO | 2011148183 | 12/2011 |
| WO | WO 2012/067160 | 5/2012 |

OTHER PUBLICATIONS

Notice of Allowance dated Nov. 4, 2014 issued in corresponding Japanese Application No. 2014-515431.
Office Action dated Nov. 13, 2014 issued in corresponding Taiwanese Application No. 101117336.
International Search Report dated Aug. 14, 2012 issued in corresponding PCT Application No. PCT/JP2012/062691.
European Extended Search Report dated Jan. 8, 2016 issued in corresponding European Application No. 12877068.2.
Office Action dated Jan. 19, 2016 issued in related Russian Application No. 2014145236.
Office Action dated Feb. 5, 2016 issued in corresponding Canadian Application No. 2870110.

\* cited by examiner

PLASTIC WORKING METHOD OF METALS AND PLASTIC WORKING APPARATUS

TECHNICAL FIELD OF THE INVENTION

This application is a national stage application of International Application No. PCT/JP2012/062691, filed May 17, 2012 which is incorporated by reference in its entirety.

The present invention relates to a plastic working method and a plastic working apparatus, in which steel including austenite can be formed while suppressing necking or breaking.

RELATED ART

Hitherto, various plastic working methods capable of improving the formability of steel have been proposed. For example, in a plastic working method disclosed in Patent Document 1, first, before the press-forming of steel, steel is pre-heated to an $AC_3$ transformation point or higher, which is an austenite single phase region of about 750° C. to 1000° C., in a heating furnace or the like. This steel in the austenite single phase state is press-formed and is quenched by being rapidly cooled using heat transfer from the steel to a mold. As a result, a press-formed product with high strength and has excellent dimensional accuracy is produced.

In addition, in a plastic working method disclosed in Patent Document 2, steel including austenite is drawn by heating a die of a mold while cooling a punch of the mold. As a result, a part of steel which forms a flange after forming is heated by heat transfer from the die so as to decrease deformation resistance thereof, and the other part of steel is cooled by heat transfer from the punch so as to increase deformation resistance thereof, thereby enabling the steel to be drawn. Accordingly, the steel can be drawn while preventing wrinkles and breaking.

In addition, in a plastic working method disclosed in Patent Document 3, in a metallographic structure of steel as a workpiece, a space factor of bainitic ferrite and/or granular bainitic ferrite as a primary phase is controlled to be 70% or more, and a space factor of retained austenite as a secondary phase is controlled to be 5% to 30%, and a C concentration in the retained austenite is controlled to be 1.0 mass % or more. As a result, the total elongation value of the steel, which is 7% at room temperature, is 20% at 250° C., and thus formability at this temperature is improved.

With these conventional technologies of the related art, the formability of steel including austenite is improved to some extent. However, currently, further improvement of formability has been required because the shapes of components are more complicated and the thicknesses thereof are more decreased.

PRIOR ART DOCUMENT

Patent Document

[Patent Document 1] Japanese Unexamined Patent Application, First Publication No. 2005-177805

[Patent Document 2] Japanese Unexamined Patent Application. First Publication No. 2007-111765

[Patent Document 3] Japanese Unexamined Patent Application. First Publication No. 2004-190050

DISCLOSURE OF THE INVENTION

Problems to be Solved by the Invention

The present invention has been made in consideration of the above-described problems, and an object thereof is to provide a plastic working method and a plastic working apparatus, in which, when steel including austenite is used as a workpiece, necking or breaking can be suppressed and the formability of the steel can be improved.

Means for Solving the Problem

The scope of the present invention is as follows.

(1) According to a first aspect of the present invention, there is provided a plastic working method of a steel including austenite, the method including: physical property analyzing process of measuring $T_\beta$, $\sigma L_\beta$, and $\sigma H_\beta$ for each of strain ratios $\beta$, when $T_\beta$ represents a strain-induced-transformation-maximum-ductility-temperature in the unit of ° C. which is changed depending on the strain ratio $\beta$. $\sigma L_\beta$ represents a standard deviation of a fitted curve of critical equivalent strain which depends on the strain ratio $\beta$ on a lower temperature side than $T_\beta$, and $\sigma H_\beta$ represents a standard deviation of a fitted curve of critical equivalent strain which depends on the strain ratio $\beta$ on a higher temperature side than $T_\beta$; deformation mode analyzing process of analyzing a strain ratio $\beta x$ to be selected from among the strain ratios $\beta$, when the strain ratio $\beta x$ is a strain ratio of an estimated breaking point which is specified during plastic deformation of the steel; heating process of heating such that a local temperature $T_{local}$ is within a first temperature range indicated by the following expression 1 after selecting $T_{\beta x}$ from among the $T_\beta$, selecting $\sigma L_{\beta x}$ from among the $\sigma L_\beta$, and selecting $\sigma H_{\beta x}$ from among the $\sigma H_\beta$ respectively, when the $T_{\beta x}$ represents a strain-induced-transformation-maximum-ductility-temperature in the unit of ° C. for the strain ratio $\beta x$, the $\sigma L_{\beta x}$ represents a standard deviation of a fitted curve of critical equivalent strain which depends on the strain ratio px on a lower temperature side than $T_{\beta x}$, the $\sigma H_{\beta x}$ represents a standard deviation of a fitted curve of critical equivalent strain which depends on the strain ratio jx on a higher temperature side than $T_{\beta x}$, and $T_{local}$ represents a local temperature in the unit of ° C. of the estimated breaking point; and working process of plastically deforming the steel after the heating:

$$T_{\beta x}-2\times\sigma L_{\beta x} \leq T_{local} \leq T_{\beta x}+1.25\times\sigma H_{\beta x} \quad \text{(Expression 1)}.$$

(2) In plastic working method according to (1), in the deformation mode analyzing process, a change in temperature $\Delta T_{local}$ may be further analyzed, when the $\Delta T_{local}$ represents a change in temperature in the unit of ° C. of the local temperature $T_{local}$ which is changed during the plastic deformation of the steel; and in the heating process, heating may be performed such that the local temperature $T_{local}$ is within a second temperature range indicated by the following expression 2:

$$T_{\beta x}-\Delta T_{local}-2\times\sigma L_{\beta x} \leq T_{local} \leq T_{\beta x}-\Delta T_{local}+1.25\times\sigma H_{\beta x} \quad \text{(Expression 2)}.$$

(3) In the plastic working method according to (1) or (2), in the heating process, at least one of the steel, a mold, and a surrounding space around the steel may be heated such that the local temperature $T_{local}$ within the temperature range.

(4) In the plastic working method according to (1) or (2), in the heating process, a heating medium may be heated such that the local temperature $T_{local}$ is within the temperature range; and in the working process, the steel may be plastically deformed using the pressure of the heating medium.

(5) In the plastic working method according to any one of (1) to (4), in the deformation mode analyzing process of analyzing the estimated breaking point, the strain ratio $\beta x$, and the change in temperature $\Delta T_{local}$ may be analyzed using a plastic working simulation.

(6) According to another aspect of the present invention, there is provided a plastic working apparatus which performs the plastic working method according to any one of (1) to (3) and (5), the apparatus including: a housing unit that accommodates the steel and a mold; a heating unit that heats at least one of the steel, the mold, and a surrounding space around the steel; and a working unit that plastically deforms the steel, which is heated by the heating unit, using the mold.

(7) The plastic working apparatus according to (6) may further include an insulating member that is arranged to cover the housing unit.

(8) The plastic working apparatus according to (6) or (7) may further include a temperature measuring unit that measures respective temperatures of the steel, the mold, and an internal space of the housing unit.

(9) According to still another aspect of the present invention, there is provided a plastic working apparatus which performs the plastic working method according any one of (1), (2), (4), and (5), the apparatus including: a housing unit that accommodates the steel and a mold; a heating medium introducing unit that introduces the heating medium into the mold; a heating unit that heats at least one of the steel, the mold, a surrounding space around the steel and the heating medium; and a working unit that plastically deforms the steel, which is heated by the heating unit, using a pressure of the heating medium.

(10) The plastic working apparatus according to (9) may further include an insulating member that is arranged to cover the housing unit.

(11) The plastic working apparatus according to (9) or (10) may further include a temperature measuring unit that measures respective temperatures of the steel, the mold, and an internal space of the housing unit, and the heating medium.

Effects of the Invention

According to the above-described aspects of the present invention, steel including austenite is plastically deformed in a temperature range including a strain-induced-transformation-maximum-ductility-temperature which corresponds to the strain ratio of an estimated breaking point of the steel. Therefore, the transformation induced plasticity phenomenon exhibited in this steel can be utilized to the maximum. As a result, it is possible to provide a plastic working method and a plastic working apparatus, in which necking or breaking can be suppressed and formability can be improved.

EMBODIMENTS OF THE INVENTION

A plastic working method and a plastic working apparatus according to embodiments of the present invention will be described in detail. However, the present invention is not limited to the configurations of the following embodiments, and various modifications can be made within a range not departing from the scope of the present invention.

First, a plastic working method according to an embodiment of the present invention will be described. In the plastic working method according to the embodiment, steel including austenite is used as a workpiece, and the transformation induced plasticity phenomenon exhibited in this steel is utilized to the maximum.

Figure 1:
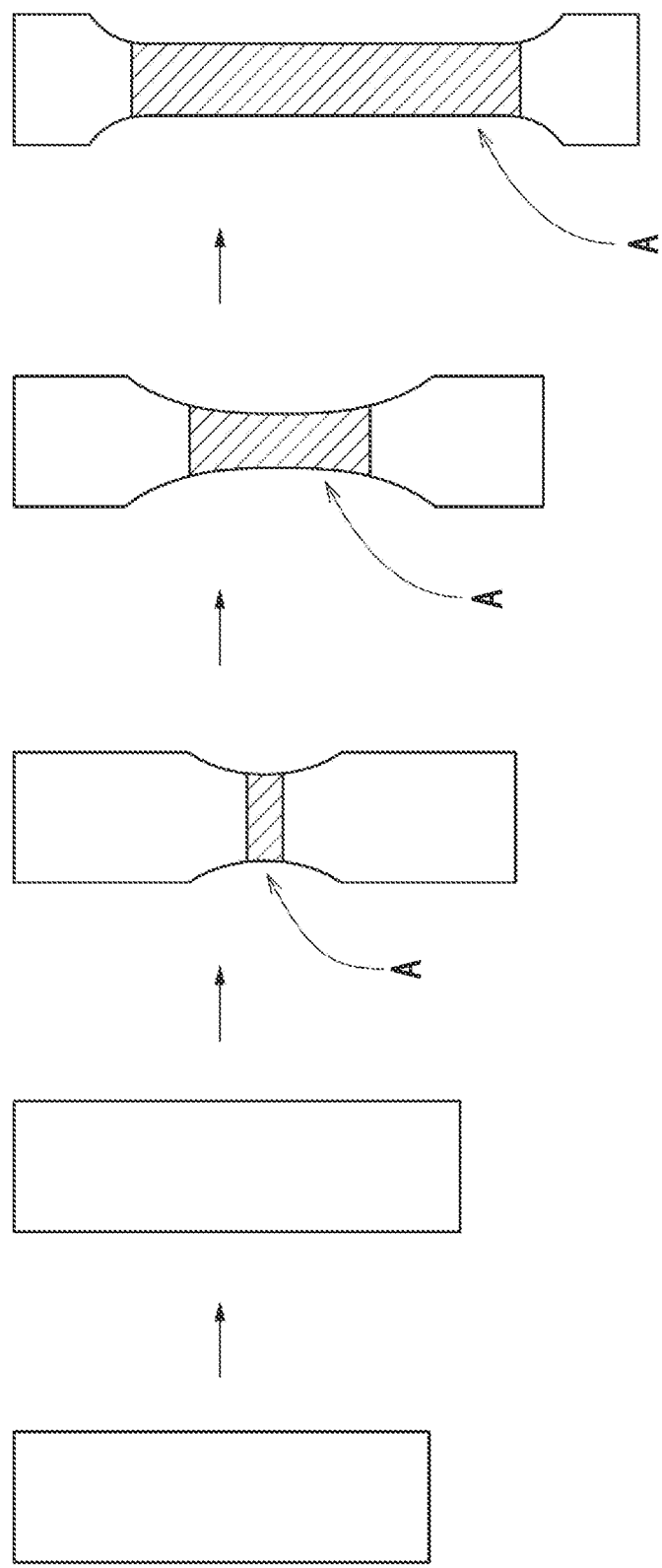
FIG. 1 is a schematic diagram showing the transformation induced plasticity phenomenon.

Here, the transformation induced plasticity (TRIP) phenomenon will be described. FIG. 1 is a schematic diagram showing the TRIP phenomenon. As shown in FIG. 1, for example, when steel including austenite (TRIP steel) is tensely deformed, necking occurs after the deformation progresses to some extent. When necking occurs, a stress applied to a neck increases. Due to this stress, stress induced transformation (indicated by A in FIG. 1) in which retained austenite is transformed into martensite occurs. Since martensite has a higher strength than other microstructures, the neck is reinforced by the stress induced transformation compared to other regions, and the deformation of the neck does not progress. As a result, deformation in the vicinity regions of the neck, where has a relatively low strength, progresses. A phenomenon in which necking caused by stress induced transformation and suppression of deformation are repeated is referred to as the transformation induced plasticity (TRIP) phenomenon. As a result, the inside of a material is uniformly deformed, and superior ductility is obtained.

However, the above-described TRIP phenomenon depends on temperature. Improvement of ductility by this TRIP phenomenon is obtained only in a specific temperature range. In addition, a temperature (hereinafter referred to as "strain-induced-transformation-maximum-ductility-temperature") at which maximum ductility is obtained by the TRIP phenomenon (stress induced transformation) depends on a chemical structure and a metallographic structure of TRIP steel. Further, as a result of a thorough study, the present inventors found that this strain-induced-transformation-maximum-ductility-temperature has a strain ratio β dependency (plastic deformation mode dependency) in which a value thereof is changed by a strain ratio β (plastic deformation mode) during plastic deformation.

Figure 2:
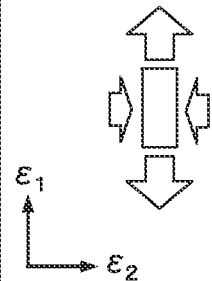
FIG. 2 is a schematic diagram showing uniaxial tension, plane strain tension, and equal biaxial tension.

The strain ratio β described herein is expressed by, when biaxial strains in a biaxial stress state are a maximum principal strain e, and a minimum principal strain $\varepsilon_2$, $\beta=\varepsilon_2 \div \varepsilon_1$. In this expression, $\varepsilon_1 \geq \varepsilon_2$. In particularly, a state where β=−0.5 is referred to as a uniaxial tension state, a state where β=0 is referred to as a plane strain tension state, and a state where β=1.0 is referred to as an equal biaxial tension state. FIG. 2 is a schematic diagram showing uniaxial tension, plane strain tension, and equal biaxial tension. As shown in FIG. 2, uniaxial tension where β=−0.5 is a deformation mode where steel is stretched in a $\varepsilon_1$ direction and is compressed in a $\varepsilon_2$ direction in the FIG. 2, and this deformation mode corresponds to plastic working such as draw forming. Plane strain tension where β=0 is a deformation mode where steel is stretched in the $\varepsilon_1$ direction and is not deformed in the $\varepsilon_2$ direction in the FIG. 2, and this deformation mode corresponds to plastic working such as bending. Equal biaxial tension where $\beta=1.0$ is a deformation mode where steel is stretched in the $\varepsilon_1$ direction and is stretched in the $\varepsilon_2$ direction in the FIG. 2, and this deformation mode corresponds to plastic working such as stretch forming.

In order to effectively utilize the TRIP phenomenon to improve plastic deformability, it is necessary that both factors be considered at the same time, the factors including: the strain-induced-transformation-maximum-ductility-temperature which is a value unique to each type of steel; and the strain ratio $\beta$ (plastic deformation mode) during plastic deformation which affects this strain-induced-transformation-maximum-ductility-temperature. However, in the above-described conventional technology of the related art, these factors are not considered. The strain-induced-transformation-maximum-ductility-temperature is a value which depends on the strain ratio $\beta$ and thus, hereinafter, will be represented by "$T_\beta$". For example, when the strain ratio $\beta$ is $-0.5$, the strain-induced-transformation-maximum-ductility-temperature thereof will be represented by $T_{-0.5}$.

Figure 3:
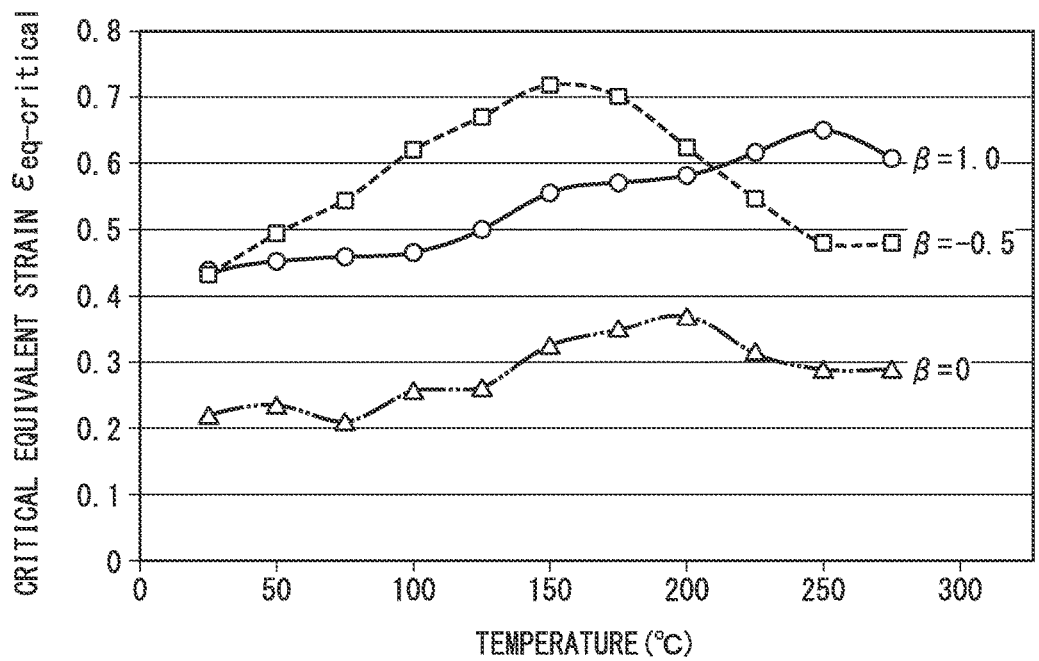
FIG. 3 is a diagram showing a temperature dependence of a critical equivalent strain of low carbon steel at each strain ratio β.

FIG. 3 shows the temperature dependence of a critical equivalent strain $\varepsilon_{eq-critical}$ at each strain ratio $\beta$ when low carbon steel is examined. In FIG. 3, a square-dot line indicates the results of $\beta=-0.5$, a triangle-two dot chain line indicates the results of $\beta=0$, and a circle-solid line indicates the results of $\beta=1.0$. In addition, an equivalent strain c refers to a strain which is calculated from the following expression A when biaxial strains in a biaxial stress state are a maximum principal strain $\varepsilon_1$ and a minimum principal strain $\varepsilon_2$. This equivalent strain $\varepsilon_{eq}$ refers to an equivalent uniaxial stress-strain component which is converted from a stress-strain component in the multiaxial stress state. This equivalent strain $\varepsilon_{eq}$ is used to compare different plastic deformation modes, that is, to compare plastic deformability (ductility) at different strain ratios $\beta$. The critical equivalent strain $\varepsilon_{eq-critical}$ refers to an equivalent strain $\varepsilon_{eq}$ at which breaking occurs in steel as a workpiece.

$$\varepsilon_{eq} = \{4 + 3 \times (\varepsilon_1^2 + \varepsilon_2^2 + \varepsilon_1\varepsilon_2)\}^{1/2} \quad \text{(Expression A)}$$

As shown in FIG. 3, the values of the critical equivalent strain $\varepsilon_{eq-critical}$ (ductility) increase in a specific temperature range. As described above, this improvement of ductility is caused by the TRIP phenomenon. In this way, the improvement of ductility by the TRIP phenomenon depends on temperature. For example, when $\beta=-0.5$, a strain-induced-transformation-maximum-ductility-temperature $T_{-0.5}$ is 150° C., and the critical equivalent strain at this temperature is the highest value.

In addition, FIG. 3 shows that the strain-induced-transformation-maximum-ductility-temperature $T_\beta$ is changed depending on the strain ratio $\beta$. For example, as described above, when $\beta=-0.5$, a strain-induced-transformation-maximum-ductility-temperature $T_{-0.5}$ is 150° C., but, when $\beta=0$, a strain-induced-transformation-maximum-ductility-temperature $T_0$ is 200° C.; and when $\beta=1.0$, a strain-induced-transformation-maximum-ductility-temperature $T_{1.0}$ is 250° C. In this way, the strain-induced-transformation-maximum-ductility-temperature $T_\beta$ depends on the strain ratio $\beta$.

Figure 4:
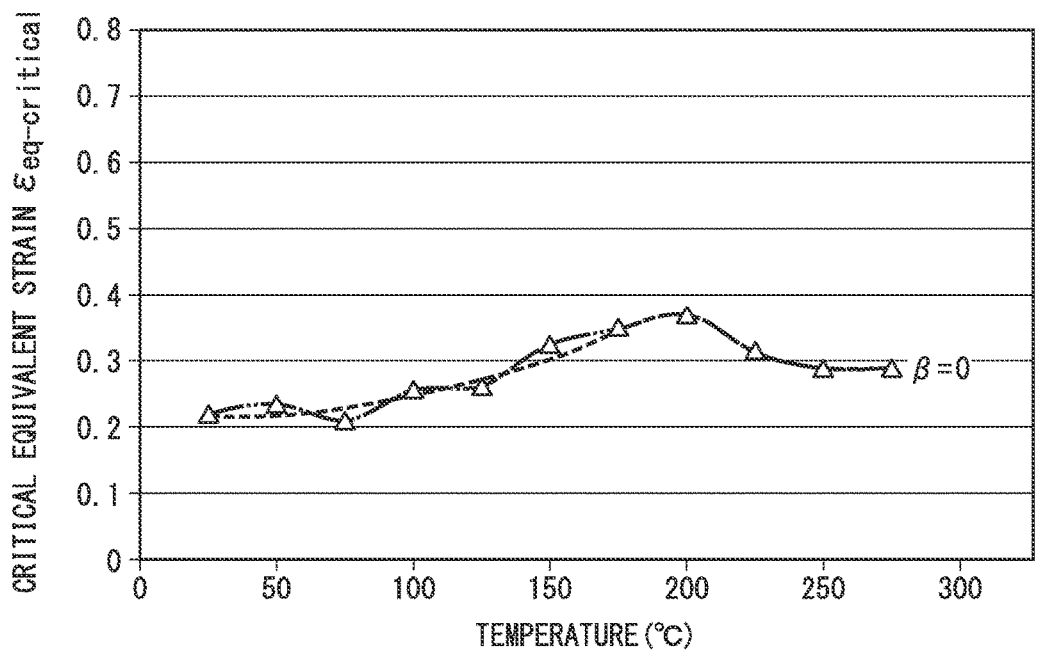
FIG. 4 is a diagram showing a normal distribution fitted curve of the temperature dependence of the critical equivalent strain when β=0 in FIG. 3.

In FIG. 4, the temperature dependence of the critical equivalent strain $\varepsilon_{eq-critical}$ when $\beta=0$ in FIG. 3 is indicated by a two-dot chain line, and a fitted curve which is plotted on the assumption that the temperature dependence follows a normal distribution curve is indicated by a dot line. As described above, when the strain ratio $\beta$ is 0, a temperature at which the critical equivalent strain $\varepsilon_{eq-critical}$ is improved to the highest value due to the TRIP phenomenon is 200° C. which is the strain-induced-transformation-maximum-ductility-temperature $T_0$. However, as shown in FIG. 4, a temperature at which the critical equivalent strain $\varepsilon_{eq-critical}$ is improved has a specific range. This temperature range in which the critical equivalent strain $\varepsilon_{eq-critical}$ is improved can be obtained from the fitted curve which is plotted on the assumption that the temperature range follows the normal distribution curve indicated by the dot line in FIG. 4.

A method of obtaining the temperature range, in which the critical equivalent strain $\varepsilon_{eq-critical}$ is improved by the above-described TRIP phenomenon, from the fitted curve (approximate function) will be described below. First, on the assumption that the temperature dependence of the critical equivalent strain $\varepsilon_{eq-critical}$ follows the normal distribution curve, the temperature dependence is approximated to a probability density function represented by the following expressions B and C. Here, the following expression B in which $\beta$ represents the strain ratio expresses an approximate function (fitted curve of critical equivalent strain which depends on the strain ratio $\beta$ on a lower temperature side than $T_\beta$) of the temperature dependence of the critical equivalent strain $\varepsilon_{eq-critical}$ on a lower temperature side than the strain-induced-transformation-maximum-ductility-temperature $T_\beta$ at which the critical equivalent strain $\varepsilon_{eq-critical}$ is improved to the highest value. The following expression C in which $\beta$ represents the strain ratio expresses an approximate function (fitted curve of critical equivalent strain which depends on the strain ratio $\beta$ on a higher temperature side than $T_\beta$) of the temperature dependence of the critical equivalent strain $\varepsilon_{eq-critical}$ on a higher temperature side than the strain-induced-transformation-maximum-ductility-temperature $T_\beta$ at which the critical equivalent strain $\varepsilon_{eq-critical}$ is improved to the highest value. In the expressions B and C, the respective symbols denote the following:

$\varepsilon_{eq-critical}$: critical equivalent strain
T: temperature
$T_\beta$: strain-induced-trans formation-maximum-ductility-temperature
$\sigma L_\beta$: standard deviation of a fitted curve of critical equivalent strain which depends on the strain ratio $\beta$ on a lower temperature side than $T_\beta$
$\sigma H_\beta$: standard deviation of a fitted curve of critical equivalent strain which depends on the strain ratio $\beta$ on a higher temperature side than $T_\beta$
e: natural logarithm
$\pi$: circular constant
$C_1$ to $C_4$: constant $$\varepsilon_{eq-critical} = C_1 \cdot \frac{1}{\sqrt{2\pi} \cdot \sigma L_\beta} e^{-\frac{(T-T_\beta)^2}{2\sigma L_\beta^2}} + C_2 \quad \text{(Expression B)}$$

$$\varepsilon_{eq-critical} = C_3 \cdot \frac{1}{\sqrt{2\pi} \cdot \sigma H_\beta} e^{-\frac{(T-T_\beta)^2}{2\sigma H_\beta^2}} + C_4 \quad \text{(Expression C)}$$

When the mathematical definition of the probability density function is taken into consideration, the temperature range in which the critical equivalent strain $\varepsilon_{eq-critical}$ is improved by the TRIP phenomenon can be expressed using $\sigma L_\beta$ and $\sigma H_\beta$ described above. That is, this temperature range can be expressed by, for example, $(T_\beta - 3 \times \sigma L_\beta)$ to $(T_\beta + 3 \times \sigma H_\beta)$, $(T_\beta - 2 \times \sigma L_\beta)$ to $(T_\beta + 2 \times \sigma H_\beta)$, or $(T_\beta - \sigma L_\beta)$ to $(T_\beta + \sigma H_\beta)$. Here, the range of $(T_\beta - 3 \times \sigma L_\beta)$ to $(T_\beta + 3 \times \sigma H_\beta)$ mathematically represents an integrated value of the probability density function being 0.9974, the range of $(T_\beta-2\times\sigma L_\beta)$ to $(T_\beta+2\times\sigma H_\beta)$ mathematically represents an integrated value of the probability density function being 0.9544, and the range of $(T_\beta-\sigma L_\beta)$ to $(T_\beta+\sigma H_\beta)$ mathematically represents an integrated value of the probability density function being 0.6826.

In this way, the temperature range in which the critical equivalent strain $\varepsilon_{eq\text{-}critical}$ is improved by the TRIP phenomenon can be expressed using $\sigma L_\beta$ and $\sigma H_\beta$ which are the standard deviations of the fitted curve (fitted curve of critical equivalent strain) which is plotted on the assumption that the temperature range follows the normal distribution curve. The values of $\sigma L_\beta$ and $\sigma H_\beta$ depend on the strain ratio $\beta$. Hereinafter, for example, when the strain ratio $\beta$ is 0. $\sigma L_\beta$ and $\sigma H_\beta$ will be represented by $\sigma L_0$ and $\sigma H_0$. When $\beta=0$, as shown in FIG. 4, the strain-induced-transformation-maximum-ductility-temperature $T_0$ is 200° C., and $\sigma L_0$ is 55° C. and $\sigma H_0$ is 19° C. as a result of analyzing the fitted curve. The analysis of the fitted curve for obtaining $\sigma L_\beta$ and $\sigma H_\beta$ can be performed using a general data analysis and graph making application or a spread sheet application having a general making function of graph.

In FIG. 4, for example, the temperature range in which the critical equivalent strain $\varepsilon_{eq\text{-}critical}$ is improved by the TRIP phenomenon can be expressed as 35° C. to 257° C. in the case of $(T_0-3\times\sigma L_0)$ to $(T_0+3\times\sigma H_0)$, 90° C. to 238° C. in the case of $(T_0-2\times\sigma L_0)$ to $(T_0+2\times\sigma H_0)$, 145° C. to 219° C. in the case of $(T_0-\sigma L_0)$ to $(T_0+\sigma H_0)$, or the like. However, as a result of a thorough study on various steels and various strain ratios, the present inventors found that, when $(T_\beta-2\times\sigma L_\beta)$ to $(T_\beta+1.25\times\sigma H_\beta)$ is adopted as the temperature range, the temperature range in which the critical equivalent strain $\varepsilon_{eq\text{-}critical}$ is improved by the above-described TRIP phenomenon can be preferably expressed without excess and deficiency. Accordingly, in the plastic working method according to the embodiment, $(T_\beta-2\times\sigma L_\beta)$ to $(T_\beta+1.25\times\sigma H_\beta)$ is adopted as the temperature range in which the critical equivalent strain $\varepsilon_{eq\text{-}critical}$ is improved by the above-described TRIP phenomenon. Otherwise, optionally, the lower limit of this temperature range may be set as $(T_\beta-1.75\times\sigma L_\beta)$, $(T_\beta-1.5\times\sigma L_\beta)$, or $(T_\beta-1.25\times\sigma L_\beta)$. Likewise, the upper limit of this temperature range may be set as $(T_\beta+1.20\times\sigma H_\beta)$, $(T_\beta+1.15\times\sigma H_\beta)$, or $(T_\beta-1010\times\sigma L_\beta)$.

When the strain ratio $\beta$ is 0, and when the temperature range is set as $(T_\beta-2\times\sigma L_0)$ to $(T_\beta+1.25\times\sigma H_0)$, the temperature range in which the critical equivalent strain $\varepsilon_{eq\text{-}critical}$ is improved by the above-described TRIP phenomenon is 90° C. to 223.75° C. That is, it can be seen that, in the case of low carbon steel, plastic working needs to be performed in a temperature range of 90° C. to 223.75° C. to improve plastic deformability in a plastic deformation mode where the strain ratio $\beta$ is 0.

It can be seen from above that the following plastic working method needs to be adopted in order to form steel (TRIP steel) including austenite as a workpiece while suppressing necking or breaking to the maximum. This method may include: (1) previously measuring the strain-induced-transformation-maximum-ductility-temperature $T_\beta$ (° C.) of steel, which is a workpiece, at each of strain ratios $\beta$, measuring the standard deviation $\sigma L_\beta$ of the fitted curve of critical equivalent strain which depends on the strain ratio $\beta$ on a lower temperature side than $T_\beta$ as the standard of $T_\beta$, and measuring the standard deviation $\sigma H_\beta$ of the fitted curve of critical equivalent strain which depends on the strain ratio $\beta$ on a higher temperature side than $T_\beta$ as the standard of $T_\beta$; (2) previously specifying a plastic deformation mode of a local region of the steel where necking or breaking is most likely to occur during forming, that is, specifying a strain ratio $\beta x$ of this local region; (3) controlling the temperature of the local region to be within a temperature range $(T_{\beta x}-2\times\sigma L_{\beta x})$ to $(T_{\beta x}+1.25\times\sigma H_{\beta x})$ suitable for the strain ratio $\beta x$; and (4) plastic working of the steel is performed under conditions where the temperature of the local region is within this temperature range. In this range, $\beta x$ represents the strain ratio $\beta$ being x ($\beta=$); $T_{\beta x}$ represents a strain-induced-transformation-maximum-ductility-temperature when the strain ratio $\beta$ is x; $\sigma L_{\beta x}$ represents a standard deviation of a fitted curve of critical equivalent strain which depends on the strain ratio $\beta x$ on a lower temperature side than $T_{\beta x}$ as the standard of $T_{\beta x}$; and $\sigma H_{\beta x}$ represents a standard deviation of a fitted curve of critical equivalent strain which depends on the strain ratio $\beta x$ on a higher temperature side than $T_{\beta x}$ as the standard of $T_{\beta x}$. $T_{\beta x}$, $\sigma L_{\beta x}$, and $\sigma H_{\beta x}$ are previously measured for each of the strain ratios $\beta$ and are included in $T_\beta$, $\sigma L_\beta$, and $\sigma H_\beta$. Accordingly, methods of measuring and analyzing $T_{\beta x}$, $\sigma L_{\beta x}$, and $\sigma H_{\beta x}$ are the same as those of $T_\beta$, $\sigma L_\beta$, and $\sigma H_\beta$.

Specifically, in the plastic working method according to the embodiment, steel including austenite is used as a workpiece, the method including: a physical property analyzing process of measuring $T_\beta$, $\sigma L_\beta$, and $\sigma H_\beta$ for each of strain ratios $\beta$, when $T_\beta$ represents a strain-induced-transformation-maximum-ductility-temperature of the steel in the unit of ° C. which is changed depending on the strain ratio $\beta$. $\sigma L_\beta$ represents a standard deviation of a fitted curve of critical equivalent strain which depends on the strain ratio $\beta$ on a lower temperature side than $T_\beta$, and $\sigma H_\beta$ represents a standard deviation of a fitted curve of critical equivalent strain which depends on the strain ratio $\beta$ on a higher temperature side than $T_\beta$; a deformation mode analyzing process of analyzing a strain ratio $\beta x$ to be selected from among the strain ratios $\beta$, when the strain ratio $\beta x$ is a strain ratio of an estimated breaking point which is specified during plastic deformation of the steel; a heating process of heating a steel such that a local temperature $T_{local}$ is within a first temperature range indicated by the following expression D after selecting the $T_{\beta x}$ from among the $T_\beta$, selecting the $\sigma L_{\beta x}$ from among the $\sigma L_\beta$, and selecting the $\sigma H_{\beta x}$ from among the $\sigma H_\beta$ respectively, when $T_{\beta x}$ represents a strain-induced-transformation-maximum-ductility-temperature of the steel in the unit of ° C. for the strain ratio $\beta x$, $\sigma L_{\beta x}$ represents a standard deviation of a fitted curve of critical equivalent strain which depends on the strain ratio $\beta x$ on a lower temperature side than $T_{\beta x}$, $\sigma H_{\beta x}$ represents the standard deviation of a fitted curve of critical equivalent strain which depends on the strain ratio $\beta i x$ on a higher temperature side than $T_{\beta s}$, and $T_{local}$ represents a local temperature in the unit of ° C. of the estimated breaking point; and a working process of plastically deforming the steel after the heating process.

$$T_{\beta x}-2\sigma L_{\beta x} \leq T_{local} \leq T_{\beta x}+1.25\times\sigma H_{\beta x} \quad \text{(Expression D)}.$$

In the physical property analyzing process, the strain-induced-transformation-maximum-ductility-temperature of the steel in the unit of ° C. used as the workpiece at each of the strain ratios $\beta$ is measured. A method of measuring the strain-induced-transformation-maximum-ductility-temperature $T_\beta$ is not particularly limited. For example, a spherical stretch forming test in which an end of a test piece is fixed while changing the horizontal and vertical dimension of the test piece may be performed at each temperature. The temperature at which the critical equivalent strain $\varepsilon_{eq\text{-}critical}$ (ductility) is improved to the highest value is set as the strain-induced-transformation-maximum-ductility-temperature $T_\beta$ at the strain ratio $\beta$ thereof. Next, for each of the steel ratios, the standard deviation of a fitted curve of critical equivalent strain which depends on the strain ratio $\beta$ on a lower temperature side than $T_\beta$ and the standard deviation of a fitted curve of critical equivalent strain which depends on the strain ratio $\beta$ on a higher temperature side than $T_\beta$ are obtained from the above-described fitted curve analysis.

In the deformation mode analyzing process, when the steel is plastically deformed, a local region (estimated breaking point) of the steel where necking or breaking is most likely to occur is specified, and a strain ratio $\beta x$ is specified as a plastic deformation mode of the local region. This strain ratio $\beta x$ is selected from among the strain ratios $\beta$ measured in the physical property analyzing process. A method of measuring the estimated breaking point and the strain ratio $\beta x$ thereof is not particularly limited. For example, a scribed circle test may be performed. The scribed circle test is a method including: depicting a circular pattern or a lattice pattern on a surface of a workpiece before working; specifying a local region (estimated breaking point) where necking or breaking is likely to occur due to plastic deformation; and measuring the pattern shape of this local region in order to specify a plastic deformation mode (strain ratio $\beta x$) of the local region. Based on the results of the scribed circle test, the plastic deformation mode of the local region can be classified as uniaxial tension ($\beta=-0.5$), a drawing region ($-0.5<\beta<0$), plane strain tension ($\beta=0$), a stretch forming region ($0<\beta<1.0$), equal biaxial tension ($\beta=1.0$) or the like.

As described above, the estimated breaking point and the strain ratio $\beta x$ thereof can be actually measured to be analyzed. However, as another analyzing method of the deformation mode analyzing process, a plastic deformation simulation using a finite element method may also be used. At this time, many plastic deformation simulation programs for computer which are commercially available may be used. By using the plastic deformation simulation, even if the inside of a workpiece is an estimated breaking point that actual measurement is difficult, the estimated breaking point can be specified and the strain ratio $\beta x$ thereof can be analyzed. Since the validity of the simulation result can be confirmed through an experiment, the estimated breaking point and the strain ratio $\beta x$ thereof can be analyzed with a minimal number of experiments.

In the heating process, a local temperature $T_{local}$ of the estimated breaking point of the steel is controlled to be within a temperature range $(T_\beta-2\times\sigma L_{\beta x})$ to $(T_{\beta x}+1.25\times\sigma H_{\beta x})$ corresponding to the strain ratio of the estimated breaking point. As described above, $(T_{\beta x}-3\times\sigma L_{\beta x})$ to $(T_{\beta x}3\times\sigma H_{\beta x})$, $(T_{\beta x}-2\times\sigma L_{\beta x})$ to $(T_{\beta x}+2\times\sigma H_{\beta x})$ as a temperature range, or the like may also be used. However, in the plastic working method according to the embodiment, $(T_{\beta x}-2\times\sigma L_{\beta x})$ to $(T_{\beta x}+1.25\times\sigma H_{\beta x})$ can be adopted as a first temperature range where plastic deformability can be improved. In order to obtain a ductility improvement effect, it is preferable that the first temperature range be optionally set to, for example, $(T_{\beta x}-\sigma L_{\beta x})$ to $(T_{\beta x}+\sigma H_{\beta x})$ or, $(T_{\beta x}-0.5\times\sigma L_{\beta x})$ to $(T_{\beta x}+0.5\times\sigma H_{\beta x})$.

In order to obtain a ductility improvement effect, it is more preferable that, in the deformation mode analyzing process, a change in temperature $\Delta T_{local}$ in the unit of ° C. that is the local temperature $T_{local}$ of the estimated breaking point which is changed by heat exchange, heating by working, or the like during plastic working is analyzed; and that, in the heating process, the local temperature $T_{local}$ be controlled to be in a second temperature range represented by the following expression E which is obtained in consideration of the change in temperature $\Delta T_{local}$ instead of the first temperature range represented by the expression D.

$$T_{\beta x}-\Delta T_{local}-2\times\sigma L_{\beta x} \leq T_{local} \leq T_{\beta x}-\Delta T_{local}+1.25\times\sigma H_{\beta x} \quad \text{(Expression E)}$$

In this way, by considering the change in temperature $\Delta T_{local}$ of the local temperature $T_{local}$ of the steel which is changed by heat exchange, heating by working, or the like during plastic working, the following effects can be obtained. For example, in plastic working in which a stain rate is slow, even if a change in temperature of the steel is large when compared with a temperature of the steel at the start of the plastic working and that at the end of the plastic working where necking or breaking is likely to occur in the steel, the local temperature $T_{local}$ of the estimated breaking point can be controlled to be within a temperature range, where the ductility improvement effect is obtained, at the end of the plastic working where plastic deformability is most needed. Alternatively, for example, in plastic working in which the stain rate is fast, even if an influence of heating by working is not negligible, the local temperature $T_{local}$ can be controlled to be within a temperature range where the ductility improvement effect is obtained. In order to obtain the ductility improvement effect, it is most preferable that the second temperature range be optionally set as, for example, $(T_{\beta x}-\Delta T_{local}-\sigma L_{\beta x})$ to $(T_{\beta x}-T_{local}+\sigma H_{\beta x})$ or $(T_{\beta x}-\Delta T_{local}-0.5\times\sigma L_{\beta x})$ to $(T_{\beta x}-\Delta T_{local}+0.5\times\sigma H_{\beta x})$.

In order to analyze the change in temperature $\Delta T_{local}$ in the deformation mode analyzing process, a thermocouple or the like may be attached to the estimated breaking point to actually measure the local temperature $T_{local}$ of the estimated breaking point during plastic deformation. In addition, with the plastic deformation simulation using the finite element method, this change in temperature $\Delta T_{local}$ may be further analyzed in addition to the estimated breaking point and the strain ratio $\beta x$ thereof.

It is preferable that, in the heating process, at least one of the steel, a mold, and a surrounding space around the steel is heated such that the local temperature $T_{local}$ of estimated breaking point is within the first temperature range or the second temperature range where the ductility improvement effect is obtained. For example, when it is determined that multiple estimated breaking points are present in the deformation mode analyzing process and that strain ratios $\beta$ between the multiple estimated breaking points are different, it is preferable that at least one of the steel, a mold, and a surrounding space around the steel be heated to control the respective temperatures of the multiple estimated breaking points to be within the first temperature range or the second temperature range suitable for the respective strain ratios $\beta$ thereof. As a result, in the respective multiple estimated breaking points, the ductility improvement effect corresponding thereto is obtained. In addition, in the heating process, at least one of the steel, a mold, and a surrounding space around the steel may be optionally cooled.

In the working process, a plastic working method is not particularly limited as long as the steel in which the local temperature $T_{local}$ of the estimated breaking point is controlled to be within the first temperature range or the second temperature range where the ductility improvement effect is obtained can be plastically deformed into a desired shape thereby. As the plastic working method, free forging, die forging, press forming using a mold, or the like may be performed.

In addition, in the heating process, a heating medium such as oil containing such as silicone oil, air, inert gas, water vapor mist, or oil mist may be heated such that the local temperature $T_{local}$ of the estimated breaking point is within the first temperature range or the second temperature range; and in the working process, the steel which is a workpiece may be plastically deformed using a pressure of the heating medium. As a result, a plastically deformed region of the workpiece is uniformly heated to be plastically deformed substantially uniformly. Therefore, effects of delaying a breaking and improving formability can be obtained.

The above-described plastic working method according to the exemplary embodiment will be summarized below.

(1) According to the embodiment, there is provided a plastic working method of steel including austenite, the method including: a physical property analyzing process of measuring $T_\beta$, $\sigma L_\beta$, and $\sigma H_\beta$ for each of strain ratios $\beta$, when $T_\beta$ represents a strain-induced-transformation-maximum-ductility-temperature of the steel in the unit of ° C. which is changed depending on the strain ratio $\beta$, $\sigma L_\beta$ represents the standard deviation of a fitted curve of critical equivalent strain which depends on the strain ratio $\beta$ on a lower temperature side than $T_\beta$, and $\sigma H_\beta$ represents the standard deviation of a fitted curve of critical equivalent strain which depends on the strain ratio $\beta$ on a higher temperature side than $T_\beta$; a deformation mode analyzing process of analyzing a strain ratio $\beta x$ to be selected from among the strain ratios $\beta$, when the strain ratio $\beta x$ is a strain ratio of an estimated breaking point which is specified during plastic deformation of the steel; a heating process of heating such that a local temperature $T_{local}$ is within a first temperature range indicated by the expression D after selecting $T_{\beta x}$ from among the $T_\beta$, selecting $\sigma L_{\beta x}$ from among the $\sigma L_\beta$, and selecting $\sigma H_{\beta x}$ from among the $\sigma H_\beta$ respectively, when $T_{\beta x}$ represents a strain-induced-transformation-maximum-ductility-temperature of the steel in the unit of ° C. for the strain ratio $\beta x$, $\sigma L_{\beta x}$ represents the standard deviation of a fitted curve of critical equivalent strain which depends on the strain ratio $\beta x$ on a lower temperature side than $T_{\beta x}$, $\sigma H_{\beta x}$ represents the standard deviation of a fitted curve of critical equivalent strain which depends on the strain ratio $\beta x$ on a higher temperature side than $T_{\beta x}$, and $T_{local}$ represents a local temperature in the unit of ° C. of the estimated breaking point; and a working process of plastically deforming the steel after the heating process.

(2) In the deformation mode analyzing process, a change in temperature $\Delta T_{local}$ may be further analyzed when $\Delta T_{local}$ represents a change in temperature in the unit of ° C. of the local temperature $T_{local}$ which is changed during the plastic deformation in the working process; and in the heating process, heating may be performed such that the local temperature $T_{local}$ is within a second temperature range indicated by the expression E.

(3) In the heating process, at least one of the steel, a mold, and a surrounding space around the steel may heated such that the local temperature $T_{local}$ is within the first temperature range or the second temperature range.

(4) In the heating process, a heating medium may be heated such that the local temperature $T_{local}$ is within the first temperature range or the second temperature range; and in the working process, the steel may be plastically deformed using a pressure of the heating medium.

(5) In the deformation mode analyzing process, the estimated breaking point and the strain ratio $\beta x$ may be analyzed using a plastic working simulation. Moreover, the change in temperature $\Delta T_{local}$ may be further analyzed using a plastic working simulation.

Next, a plastic working apparatus according to an embodiment of the present invention will be described.

First Embodiment

Figure 5:
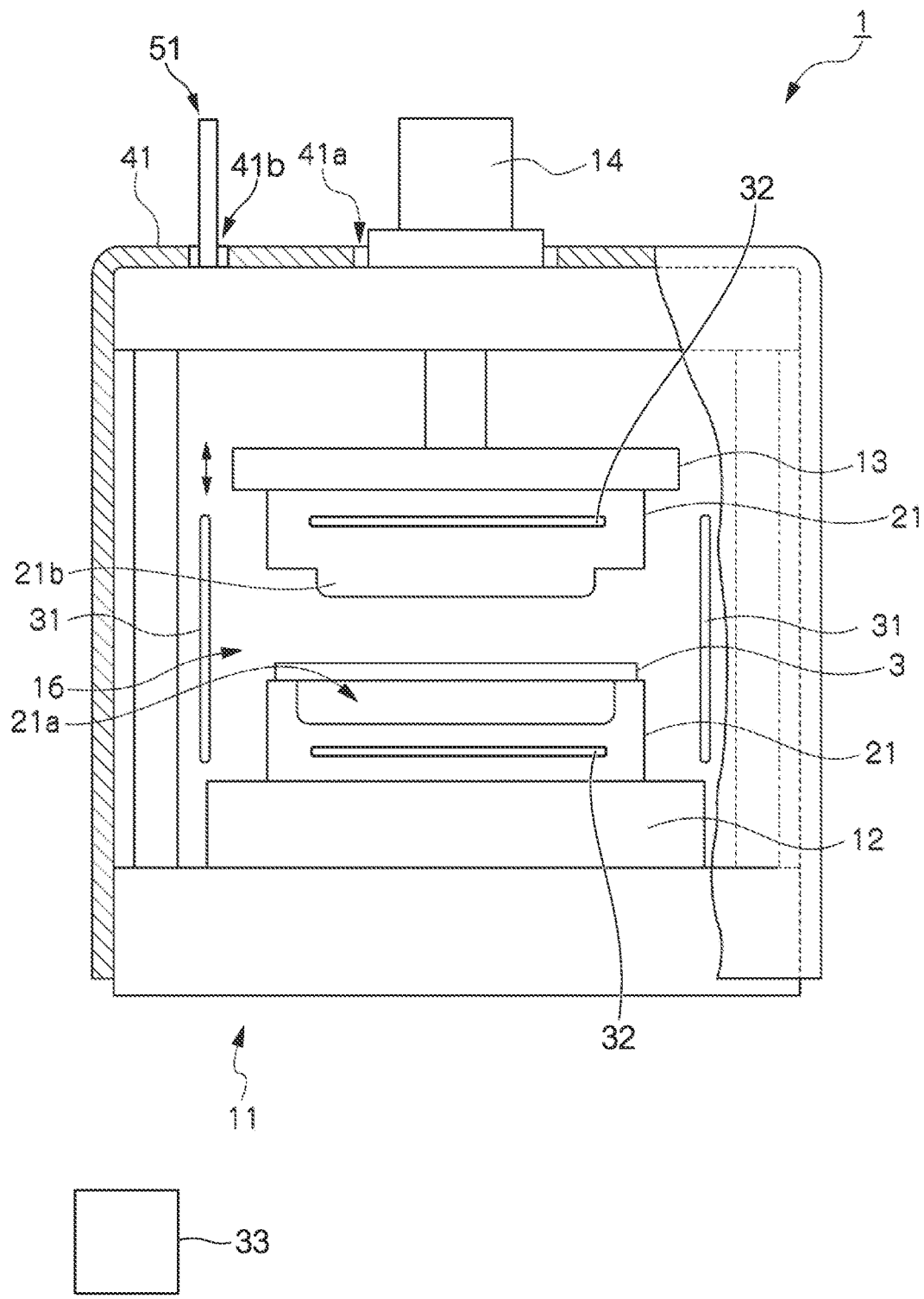
FIG. 5 is a partially cutaway front view showing a schematic configuration of a plastic working apparatus according to an embodiment of the present invention.

A plastic working apparatus according to a first embodiment of the present invention will be described. FIG. 5 is a partially cutaway front view showing a schematic configuration of the plastic working apparatus according to the first embodiment of the present invention.

A configuration of a working unit of the plastic working apparatus 1 according to the embodiment will be described below. A main body frame 11 is provided to attach the respective components, such as a pair of molds 21, constituting the plastic working apparatus 1 thereto. A bolster 12 is disposed in an inner lower portion of the main body frame 11, and a slide 13 is disposed in an inner upper portion thereof. The slide 13 is configured to be vertically driven by a slide driving device 14 such as a motor or a cylinder disposed above the main body frame 11. An upper mold 21 is attached to a lower surface of the slide 13, and a lower mold 21 is attached to an upper surface of the bolster 12. As a result, the plastic working apparatus 1 is attached to the main body frame 11 in a state where the pair of molds 21 is arranged opposite each other and is configured to plastically deform a workpiece 3 between the pair of molds 21 by the slide 13 vertically moving. The configurations of the main body frame 11 and the like of the plastic working apparatus 1 are not particularly limited as long as the workpiece 3 can be plastically deformed by the pair of molds 21.

The pair of molds 21 performs plastic working such as bending, drawing, flange forming, burring, or stretch forming on the workpiece 3 disposed between the pair of molds 21. The shape of the pair of molds 21 is adjusted according to the type of plastic working and the shape of a formed product, and a well-known configuration is used as a configuration of the pair of molds 21. The pair of molds 21 is configured to bend the work piece 3, for example, by the upper mold 21 being driven such that the workpiece 3 placed on the lower mold 21 is inserted into a concave portion 21a of the lower mold 21 by a convex portion 21b of the upper mold 21. The pair of molds 21 may be provided with, for example, a blank holder for drawing. The pair of molds 21 may have a configuration in which both the upper mold 21 and the lower mold 21 are provided with the concave portion 21a to die-forge the workpiece 3.

The plastic working apparatus 1 according to the embodiment includes, as a heating unit, a heater 31 that heats an inside atmosphere of a space 16 including the workpiece 3 and the pair of molds 21 and a heater 32 that heats the pair of molds 21. In addition, the heating unit includes a heating furnace 33 that is provided outside the plastic working apparatus 1 and heats the workpiece 3. The plastic working apparatus 1 may be configured to include at least one of the heater 31, the heater 32, and the heating furnace 33. In a configuration including the heater 31, the heater 31 heats the inside atmosphere of the space 16 and thus can heat intentionally such that a temperature difference between the workpiece 3 and the space 16 is relatively small or large. In a configuration including the heater 32, the heater 32 heats the pair of molds 21 and thus can heat intentionally such that a temperature difference between the workpiece 3 and the molds 21 is relatively small or large. In a configuration including the heating furnace 33, a temperature of the workpiece 3 before being installed inside the space 16 of the plastic working apparatus 1 can be controlled to a desired temperature. In this way, at least one of the heater 31, the heater 32, and the heating furnace 33 is used. Therefore, even if multiple estimated breaking points are present in the workpiece 3, the respective temperatures of the multiple estimated breaking points can be controlled to temperatures corresponding to the estimated breaking points. In addition, in the heating unit, optionally, at least one of the workpiece 3, the molds 21, and the space 16 may be cooled.

In addition, the plastic working apparatus 1 includes a cover 41 (heat insulating cover, insulating member) so as to cover the space 16. The space 16 covered with the cover 41 functions as a housing unit that accommodates the workpiece 3.

The heater 31 only needs to heat the inside atmosphere 16 of the space 16 including the workpiece 3 and the pair of molds 21 and the heater 32 only needs to heat the molds 21 such that the estimated breaking point of the workpiece 3 is heated to the first temperature range or the second temperature range. Accordingly, the positions and the configurations of the heaters are not limited and may be configured of, for example, an induction heating coil, a burner, or the like in addition to an electric heater. For example, the heater 31 is attached to the main body frame 11, and the heater 32 is attached to the inside of the molds 21. In addition, optionally, the heater 31, the heater 32, and the heating furnace 33 may have a cooling function of cooling the workpiece 3 to room temperature or lower. In this case, even if the strain-induced-transformation-maximum-ductility-temperature $T_\beta$ of the workpiece 3 is room temperature or lower, the temperature of the estimated breaking point of the workpiece 3 can be controlled to be within the first temperature range or the second temperature range. Therefore, the above configuration is preferable.

The cover 41 is disposed to surround the space 16 including the workpiece 3 and the pair of molds 21 and to prevent heat radiation from the inside atmosphere of the space 16 to the outside or prevent infiltration of outside air to the inside of the space 16. The cover 41 is formed of an insulating member which is a material with high thermal insulation. For example, a heat resisting material such as glass wool or aluminum film laminate is attached to the inside of a metal outer frame having a water cooling function. Further, the cover 41 has an opening and a door which is not shown through which the workpiece is taken in and out. In the embodiment, the cover 41 is formed in a box shape and is attached to the main body frame 11 so as to cover sides and an upper of the main body frame 11. However, the shape, the position, and the attachment method of the cover 41 are not particularly limited as long as the cover 41 can surround the space 16 including at least the pair of molds 21. In the embodiment, an insertion hole 41a into which the slide driving device 14 protruding from the upper of the main body frame 11 is inserted, and an insertion hole 41b into which an inert gas introducing unit described below for introducing inert gas is inserted are formed in the cover 41.

It is preferable that the plastic working apparatus 1 according to the embodiment further include an inert gas introducing unit 51. The inert gas introducing unit 51 includes a gas cylinder and a metal pipe, which are not shown, to substitute the inside atmosphere of the space 16 with, for example, inert gas such as Ar or $N_2$. Using the inert gas introducing unit 51, the surface oxidation of the workpiece 3 can be minimized. The shape, the position, and the attachment method of the inert gas introducing unit 51 are not particularly limited. In the embodiment, inert gas such as Ar or $N_2$ is blown from the metal pipe which is attached to the insertion hole 41b formed in the cover 41. In order to suppress the surface oxidation of the workpiece 3, it is more preferable that the inert gas introducing unit 51 further include a vacuum pump which is not shown.

In addition, it is preferable that the plastic working apparatus 1 according to the embodiment further include a temperature measuring unit. The temperature measuring unit includes a thermometer and a display device, which are not shown, which are attached to each of the workpiece 3, the molds 21, and the space 16, so as to independently measure the respective temperatures of the workpiece 3, the molds 21, and the space 16. The shape, the position, and the attachment method of the temperature measuring unit are not particularly limited. As the thermometer, for example, a contact thermocouple thermometer or an infrared thermometer may be used. In the embodiment, a thermocouple is used as the temperature measuring unit.

The above-described plastic working apparatus according to the exemplary embodiment will be summarized below.

(6) The plastic working apparatus according to the first embodiment of the present invention includes: the housing unit that accommodates the workpiece 3 (steel) and the pair of molds 21; the heating unit that heats at least one of the workpiece 3 (steel), the pair of molds 21, and the space 16 (surrounding space around the steel) such that the local temperature $T_{local}$ of the estimated breaking point of the workpiece 3 (steel) is within the first temperature range and the second temperature range; and the working unit that plastically deforms the workpiece 3 (steel), which is heated by the heating unit, using the pair of molds 21.

(7) The plastic working apparatus further includes the cover 41 (insulating member) that is arranged to cover the housing unit.

(8) The plastic working apparatus further includes the temperature measuring unit that measures respective temperatures of the workpiece 3 (steel), the pair of molds 21, and the space 16 (internal space of the housing unit).

Second Embodiment

Figure 6:
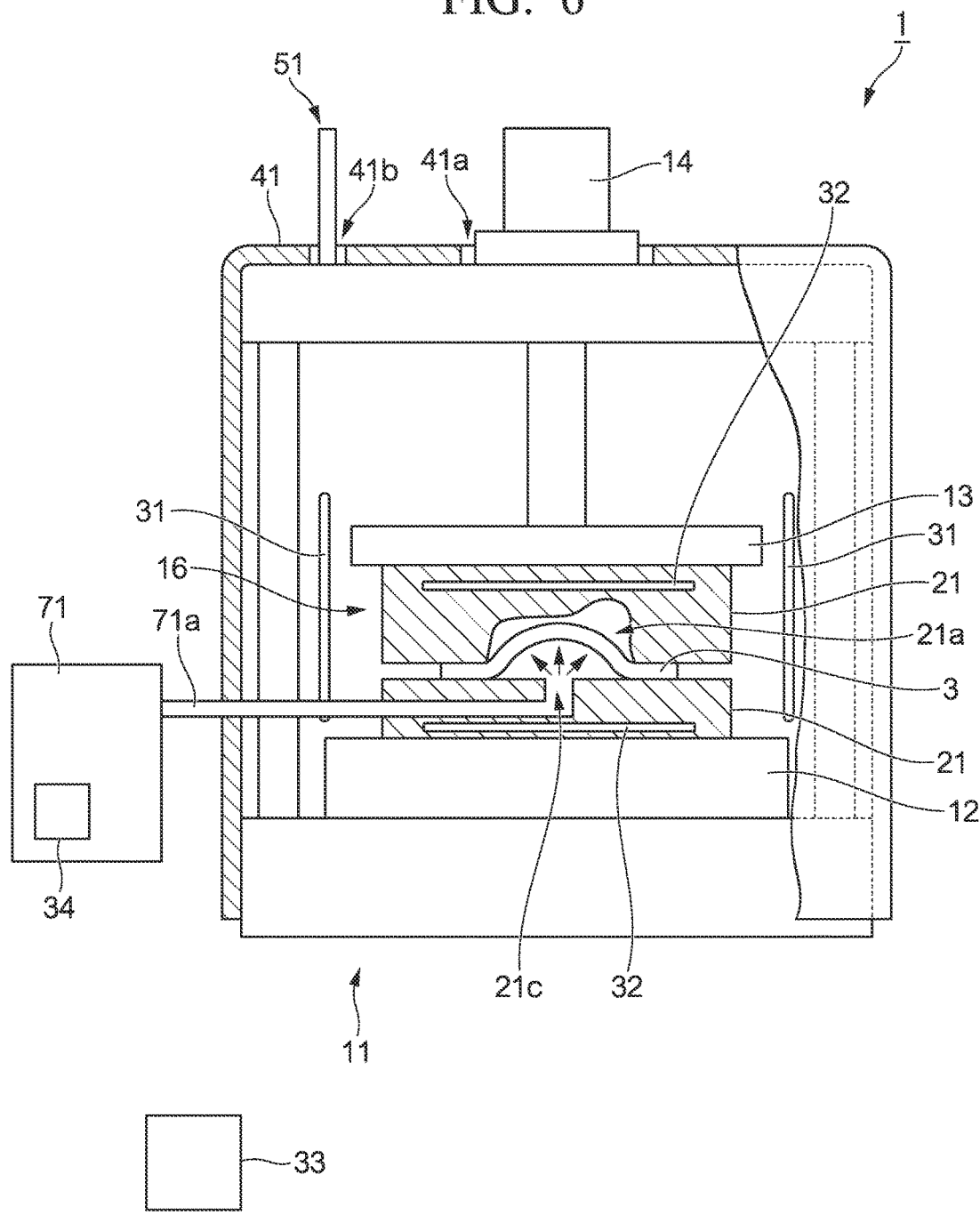
FIG. 6 is a partially cutaway front view showing a schematic configuration of a plastic working apparatus according to another embodiment of the present invention.

Next, a plastic working apparatus according to a second embodiment of the present invention will be described. FIG. 6 is a partially cutaway front view showing a schematic configuration of the plastic working apparatus according to the second embodiment of the present invention.

Since this second embodiment has a difference in a structure of the molds 21 from the first embodiment, this difference will be mainly described. The other structures are the same as those of the first embodiment, and thus the description thereof will not be repeated here.

In the plastic working apparatus 1 according to the embodiment, the workpiece 3 disposed between the pair of molds 21 are plastically deformed by the pair of molds 21 and a heating medium. For example, the heating medium whose pressure and temperature are controlled by a heating medium introducing unit 71 is introduced through a pipe 71a from a heating medium introduction hole 21c provided in the lower mold 21. The workpiece 3 which is fixed between the upper mold 21 and the lower mold 21 by the slide driving device 14 is pressed into the concave portion 21 provided in the upper mold 21 by a pressure of the heating medium. As a result, the workpiece 3 is formed in a desired shape.

As the heating medium, for example, oil such as silicone oil or gas such as air, inert gas, water vapor mist, or oil mist can be used. In addition, the heating medium introducing unit 71 is not particularly limited as long as it can control the pressure and the temperature of the heating medium.

The plastic working apparatus 1 according to the embodiment includes, as a heating unit, the heater 31 that heats the inside atmosphere of the space 16 including the workpiece 3 and the pair of molds 21, the heater 32 that heats the pair of molds 21, and a heater 34 that heats the heating medium. In addition, the heating unit includes the heating furnace 33 that is provided outside the plastic working apparatus 1 and heats the workpiece 3. By using at least one of the heater 31, the heater 32, the heater 34, and the heating furnace 33, the temperature of the estimated breaking point of the workpiece 3 can be controlled to a temperature corresponding to the estimated breaking point. Even if multiple estimated breaking points are present in the workpiece 3, the respective temperatures of the multiple estimated breaking points can be more preferably controlled to temperatures corresponding to the estimated breaking points by controlling the above-described four heating sources. In addition, optionally, the heater 31, the heater 32, the heater 34, and the heating furnace 33 may have a cooling function of cooling the workpiece to room temperature or lower. In this case, even if the strain-induced-transformation-maximum-ductility-temperature $T_\beta$ of the workpiece 3 is room temperature or lower, the temperature of the estimated breaking point of the workpiece 3 can be controlled to be within the first temperature range or the second temperature range. Therefore, the above configuration is preferable.

In addition, the plastic working apparatus 1 according to the embodiment includes the cover 41 (heat insulating cover, insulating member) so as to cover the space 16. The space 16 covered with the cover 41 functions as the housing unit that accommodates the workpiece 3.

In addition, it is preferable that the plastic working apparatus 1 according to the embodiment further include the temperature measuring unit. The temperature measuring unit includes a thermometer and a display device, which are not shown, which are attached to each of the workpiece 3, the molds 21, the space 16, and the heating medium introducing unit 71, so as to independently measure the respective temperatures of the workpiece 3, the molds 21, the space 16, and the heating medium. The shape, the position, and the attachment method of the temperature measuring unit are not particularly limited. As the thermometer, for example, a contact thermocouple thermometer or an infrared thermometer may be used.

The above-described plastic working apparatus according to the exemplary embodiment will be summarized below.

(9) The plastic working apparatus according to the second embodiment of the present invention includes: the housing unit that accommodates the workpiece 3 (steel) and the pair of molds 21; the heating medium introducing unit that introduces the heating medium into the molds 21; the heating unit that heats at least one of the workpiece 3 (steel), the pair of molds 21, the space 16 (surrounding space around the steel), and the heating medium such that the local temperature $T_{local}$ of the estimated breaking point of the workpiece 3 (steel) is within the first temperature range and the second temperature range; and the working unit that plastically deforms the workpiece 3 (steel), which is heated by the healing unit, using a pressure of the heating medium.

(10) The plastic working apparatus further includes the cover 41 (insulating member) that is arranged to cover the housing unit.

(11) The plastic working apparatus further includes the temperature measuring unit that measures respective temperatures of the workpiece 3 (steel), the pair of molds 21, the space 16 (internal space of the housing unit), and the heating medium.

Example 1

Next, examples of the present invention will be described. However, conditions of the examples are condition examples for confirming the operability and the effects of the present invention, and the present invention is not limited to these condition examples. In the present invention, various conditions can be adopted within the scope of the present invention as long as the object of the present invention is achieved.

In the physical property analyzing process, using steel including austenite (Examples) and steel not including austenite (Comparative Examples), each strain ratio β and the critical equivalent strain $\varepsilon_{eq\text{-}critical}$ at each temperature were measured. As a method of measuring each strain ratio β and the critical equivalent strain $\varepsilon_{eq\text{-}critical}$ at each temperature, a spherical stretch forming test in which an end of a test piece was fixed while changing the horizontal and vertical dimension of the test piece was performed at each temperature. The critical equivalent strain $\varepsilon_{eq\text{-}critical}$ was calculated from a strain when necking or breaking occurs.

Table 1 shows the measurement results of each strain ratio β and the critical equivalent strain $\varepsilon_{eq\text{-}critical}$ at each temperature. For example, in Example 1, when β=−0.5, a strain-induced-transformation-maximum-ductility-temperature $T_{-0.5}$ at which the critical equivalent strain $\varepsilon_{eq\text{-}critical}$ was maximum was 75° C.; and when β=1.0, a strain-induced-transformation-maximum-ductility-temperature $T_{1.0}$ was 150° C. In Example 3, when β=−0.5, a strain-induced-transformation-maximum-ductility-temperature $T_{-0.5}$ was 150° C.; and when β=1.0, a strain-induced-transformation-maximum-ductility-temperature $T_{1.0}$ was 250° C. In this way, in the steel including austenite (Examples), the critical equivalent strain $\varepsilon_{eq\text{-}critical}$ is changed depending on the type of steel, the working temperature, and the strain ratio β. On the other hand, in Comparative Example 6, as shown in Table 1, a temperature at which the critical equivalent strain $\varepsilon_{eq\text{-}critical}$ was maximum does not depend on the strain ratio β. That is, the strain-induced-transformation-maximum-ductility-temperature $T_\beta$ does not depend on the strain ratio β. This is because the TRIP phenomenon does not occur in the steel not including austenite (Comparative Examples).

Table 2 shows a standard deviation $\sigma L_\beta$ of a fitted curve of critical equivalent strain which depends on the strain ratio β on a lower temperature side than $T_\beta$; a standard deviation $\sigma H_\beta$ of a fitted curve of critical equivalent strain which depends on the strain ratio f on a higher temperature side than $T_\beta$, in which $T_\beta$ represents the strain-induced-transformation-maximum-ductility-temperature at each strain ratio which is obtained by analyzing the fitted curve (approximate function) using the results of Table 1. In this way, by analyzing $\sigma L_\beta$ and $\sigma H_\beta$ for each strain ratio, the temperature range in which plastic deformability can be improved at each strain ratio can be determined. For example, in Example 3, when β=0, $2\times\sigma L_0=110°$ C. and $1.25\times\sigma H_0=24°$ C. Therefore, based on the strain-induced-transformation-maximum-ductility-temperature $T_\beta$, the temperature range in which the critical equivalent strain $\varepsilon_{eq\text{-}critical}$ is improved by the TRIP phenomenon can be determined to be 90° C. to 224° C.

Figure 7:
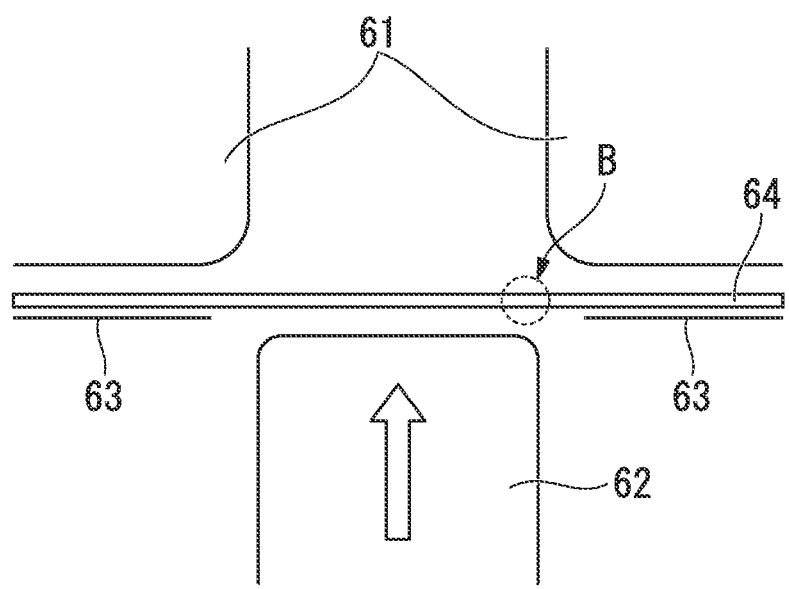
FIG. 7 is a schematic diagram showing forming by square cylinder drawing.

Next, in the deformation mode analyzing process, an estimated breaking point of a workpiece and the strain ratio β of this estimated breaking point were analyzed during forming by square cylinder drawing. FIG. 7 is a schematic diagram showing forming by square cylinder drawing. As shown in FIG. 7 using dies 61 having a size of 80 mm×80 mm, a square cylinder-shaped punch 62 having a size of 75 mm×75 mm, and a holder 63, forming by square cylinder drawing was performed on a blank 64 (workpiece). Analysis regarding this forming by square cylinder drawing was performed in a scribed circle test. It was able to be specified in the forming by square cylinder drawing from the analysis results of the scribed circle test that a B portion of the blank 64 (workpiece) shown in FIG. 7 was an estimated breaking point and that a plastic deformation mode of the B portion was a uniaxial tension state where the strain ratio β was −0.5.

Next, in the heating process, using the steel of Example 3 of Table 1 as a workpiece, the temperature of at least one of the steel, the mold, and the surrounding space was controlled such that the local temperature $T_{local}$ of the estimated breaking point was within a range of 25° C. to 250° C. Next, in the working process, the steel of Example 3 whose temperature was controlled in the heating process was formed by square cylinder drawing.

Table 3 shows the results of the forming by square cylinder drawing in which the steel of Example 3 as the workpiece was heated such that the local temperature $T_{local}$ of the estimated breaking point was within a range of 25° C. to 250° C. The drawing height shown in Table 3 refers to the height at which the workpiece can be drawn without necking or breaking, and the higher the value, the higher the formability.

As shown in Table 1, in the steel of Example 3, when the strain ratio β was −0.5, the strain-induced-transformation-maximum-ductility-temperature $T_{-0.5}$ was 150° C. In addition, as shown in Table 2, in the case of $β_{-0.5}$, $2×σL_{-0.5}$=110° C. and $1.25×σH_{-0.5}$=69° C. That is, in the forming by square cylinder drawing, it was expected that when the local temperature $T_{local}$ of the estimated breaking point was within a range of 40° C. to 219° C. (first temperature range), the drawing height would be high; and that when $T_{local}$=150° C., the drawing height would be highest. Actually, as shown in Table 3, it was able to be confirmed that, when the local temperature $T_{local}$ of the estimated breaking point was within the first temperature range of 50° C. to 200° C., the drawing height was sufficiently high. In addition, when the local temperature $T_{local}$ of the estimated breaking point was 150° C., the drawing height was highest. The formability of a case where the forming by square cylinder drawing was performed in the above-described temperature range was improved to be about two times the formability of a case where the forming by square cylinder drawing was performed at 25° C. and 250° C. although the same workpiece was used. In this way, with the plastic working method according to the above embodiment of the present invention, necking or breaking can be suppressed, and formability can be improved.

TABLE 1

| | | | Properties of Workpiece | | | | | |
|---|---|---|---|---|---|---|---|---|
| | | | Strain Ratio β: ε 2/ε 1 | | | | | |
| | Austenite Fraction/% | Temperature/ ° C. | β = −0.5 Critical Equivalent Strain | β = −0.25 Critical Equivalent Strain | β = 0 Critical Equivalent Strain | β = 0.25 Critical Equivalent Strain | β = 0.5 Critical Equivalent Strain | β = 1 Critical Equivalent Strain |
| Example 1 | 100 | 25 | 0.602 | 0.635 | 0.558 | 0.607 | 0.707 | 1.004 |
| | | 50 | 0.668 | 0.729 | 0.631 | 0.634 | 0.753 | 1.026 |
| | | 75 | 0.764 | 0.753 | 0.681 | 0.673 | 0.769 | 1.059 |
| | | 100 | 0.72 | 0.775 | 0.722 | 0.703 | 0.794 | 1.084 |
| | | 125 | 0.713 | 0.754 | 0.667 | 0.727 | 0.834 | 1.151 |
| | | 150 | 0.703 | 0.685 | 0.596 | 0.661 | 0.817 | 1.208 |
| | | 175 | 0.649 | 0.618 | 0.477 | 0.621 | 0.756 | 1.124 |
| | | 200 | 0.638 | 0.548 | 0.486 | 0.529 | 0.618 | 1.066 |
| Example 2 | 100 | 25 | 0.682 | 0.702 | 0.681 | 0.665 | 0.827 | 0.911 |
| | | 50 | 0.712 | 0.704 | 0.715 | 0.725 | 0.907 | 0.949 |
| | | 75 | 0.698 | 0.683 | 0.722 | 0.764 | 0.921 | 0.983 |
| | | 100 | 0.687 | 0.624 | 0.669 | 0.798 | 0.953 | 1.007 |
| | | 125 | 0.597 | 0.598 | 0.631 | 0.767 | 0.961 | 1.069 |
| | | 150 | 0.501 | 0.571 | 0.59 | 0.739 | 0.948 | 1.087 |
| | | 175 | 0.475 | 0.567 | 0.538 | 0.882 | 0.847 | 0.971 |
| | | 200 | 0.457 | 0.51 | 0.455 | 0.583 | 0.759 | 0.808 |
| Example 3 | 17.6 | 25 | 0.43 | 0.34 | 0.219 | 0.278 | 0.35 | 0.441 |
| | | 50 | 0.493 | 0.372 | 0.234 | 0.291 | 0.378 | 0.453 |
| | | 75 | 0.544 | 0.401 | 0.209 | 0.295 | 0.404 | 0.48 |
| | | 100 | 0.621 | 0.423 | 0.254 | 0.317 | 0.431 | 0.466 |
| | | 125 | 0.671 | 0.467 | 0.263 | 0.351 | 0.468 | 0.501 |
| | | 150 | 0.718 | 0.624 | 0.324 | 0.378 | 0.498 | 0.556 |
| | | 175 | 0.702 | 0.579 | 0.348 | 0.389 | 0.51 | 0.571 |
| | | 200 | 0.622 | 0.51 | 0.37 | 0.391 | 0.555 | 0.583 |
| | | 225 | 0.547 | 0.471 | 0.312 | 0.421 | 0.578 | 0.617 |
| | | 250 | 0.48 | 0.434 | 0.287 | 0.407 | 0.547 | 0.651 |
| | | 275 | 0.48 | 0.434 | 0.287 | 0.387 | 0.521 | 0.608 |
| Example 4 | 12 | 25 | 0.416 | 0.372 | 0.202 | 0.295 | 0.375 | 0.527 |
| | | 50 | 0.412 | 0.392 | 0.217 | 0.304 | 0.412 | 0.585 |
| | | 75 | 0.41 | 0.391 | 0.216 | 0.314 | 0.439 | 0.574 |
| | | 100 | 0.403 | 0.368 | 0.216 | 0.317 | 0.458 | 0.566 |
| | | 125 | 0.463 | 0.37 | 0.246 | 0.33 | 0.454 | 0.561 |
| | | 150 | 0.492 | 0.4 | 0.263 | 0.332 | 0.424 | 0.53 |
| | | 175 | 0.529 | 0.406 | 0.261 | 0.349 | 0.471 | 0.601 |
| | | 200 | 0.51 | 0.416 | 0.258 | 0.355 | 0.491 | 0.65 |
| | | 225 | 0.497 | 0.41 | 0.304 | 0.386 | 0.624 | 0.708 |
| | | 250 | 0.481 | 0.389 | 0.271 | 0.366 | 0.551 | 0.764 |
| | | 275 | 0.47 | 0.38 | 0.251 | 0.359 | 0.514 | 0.732 |
| Example 5 | 4.6 | 0 | 0.405 | 0.398 | 0.347 | 0.346 | 0.451 | 0.536 |
| | | 25 | 0.389 | 0.405 | 0.357 | 0.37 | 0.484 | 0.651 |
| | | 50 | 0.384 | 0.384 | 0.326 | 0.41 | 0.549 | 0.78 |
| | | 75 | 0.375 | 0.381 | 0.324 | 0.387 | 0.671 | 0.814 |

TABLE 1-continued

Properties of Workpiece

Strain Ratio β: ε 2/ε 1

| | Austenite Fraction/% | Temperature/ ° C. | β = −0.5 Critical Equivalent Strain | β = −0.25 Critical Equivalent Strain | β = 0 Critical Equivalent Strain | β = 0.25 Critical Equivalent Strain | β = 0.5 Critical Equivalent Strain | β = 1 Critical Equivalent Strain |
|---|---|---|---|---|---|---|---|---|
| | | 100 | 0.37 | 0.365 | 0.312 | 0.375 | 0.556 | 0.84 |
| | | 150 | 0.357 | 0.344 | 0.292 | 0.365 | 0.604 | 0.64 |
| | | 200 | 0.325 | 0.343 | 0.232 | 0.305 | 0.409 | 0.58 |
| | | 225 | 0.317 | 0.321 | 0.201 | 0.278 | 0.387 | 0.586 |
| | | 250 | 0.31 | 0.318 | 0.196 | 0.289 | 0.376 | 0.587 |
| Comparative Example 6 | 0 | 25 | 0.752 | 0.707 | 0.514 | 0.67 | 0.82 | 1.034 |
| | | 50 | 0.715 | 0.672 | 0.489 | 0.638 | 0.801 | 0.974 |
| | | 75 | 0.684 | 0.643 | 0.468 | 0.512 | 0.784 | 0.927 |
| | | 100 | 0.642 | 0.604 | 0.439 | 0.584 | 0.75 | 0.901 |
| | | 125 | 0.628 | 0.590 | 0.429 | 0.546 | 0.723 | 0.882 |
| | | 150 | 0.597 | 0.561 | 0.408 | 0.525 | 0.699 | 0.845 |
| | | 175 | 0.557 | 0.524 | 0.381 | 0.481 | 0.656 | 0.841 |
| | | 200 | 0.529 | 0.497 | 0.362 | 0.463 | 0.62 | 0.819 |
| | | 225 | 0.518 | 0.487 | 0.354 | 0.45 | 0.576 | 0.796 |
| | | 250 | 0.497 | 0.467 | 0.340 | 0.438 | 0.547 | 0.778 |

TABLE 2

Properties of Workpiece

Optimum Temperature $T_\beta$ Of Stress Induced Transformation

| | Austenite Fraction/% | Optimum Temperature $T_\beta$ Of Stress Induced Transformation | Strain Ratio β | | | | | |
|---|---|---|---|---|---|---|---|---|
| | | | β = −0.5 | β = −0.25 | β = 0 | β = 0.25 | β = 0.5 | β = 1.0 |
| Example 1 | 100 | Optimum Temperature $T_\beta$ Of Stress Induced Transformation (° C.) | 75 | 100 | 100 | 125 | 125 | 150 |
| | | 2 × σ $L_\beta$ (° C.) | 90 | 130 | 100 | 140 | 130 | 86 |
| | | 1.25 × σ $H_\beta$ (° C.) | 75 | 58 | 44 | 50 | 64 | 38 |
| Example 2 | 100 | Optimum Temperature $T_\beta$ Of Stress Induced Transformation (° C.) | 50 | 50 | 75 | 100 | 125 | 150 |
| | | 2 × σ $L_\beta$ (° C.) | 90 | 160 | 140 | 100 | 150 | 100 |
| | | 1.25 × σ $H_\beta$ (° C.) | 76 | 88 | 68 | 64 | 44 | 50 |
| Example 3 | 17.5 | Optimum Temperature $T_\beta$ Of Stress Induced Transformation (° C.) | 150 | 175 | 200 | 225 | 225 | 250 |
| | | 2 × σ $L_\beta$ (° C.) | 110 | 106 | 110 | 140 | 160 | 150 |
| | | 1.25 × σ $H_\beta$ (° C.) | 69 | 56 | 24 | 38 | 38 | 19 |
| Example 4 | 12 | Optimum Temperature $T_\beta$ Of Stress Induced Transformation (° C.) | 175 | 200 | 225 | 225 | 250 | 250 |
| | | 2 × σ $L_\beta$ (° C.) | 62 | 120 | 160 | 140 | 180 | 120 |
| | | 1.25 × σ $H_\beta$ (° C.) | 62 | 38 | 25 | 25 | 19 | 19 |
| Example 5 | 4.5 | Optimum Temperature $T_\beta$ Of Stress Induced Transformation (° C.) | 0 | 25 | 25 | 50 | 75 | 100 |
| | | 2 × σ $L_\beta$ (° C.) | 60 | 40 | 30 | 30 | 50 | 90 |
| | | 1.25 × σ $H_\beta$ (° C.) | 150 | 114 | 114 | 100 | 75 | 38 |

TABLE 3

| | Local Temperature $T_{local}$ of Estimated Breaking Point | Drawing Height mm |
|---|---|---|
| Example 3 | 25 | 27.7 |
| | 50 | 37.1 |
| | 100 | 50 |
| | 125 | 50 |
| | 150 | 50 |
| | 175 | 47.5 |
| | 200 | 43.5 |
| | 250 | 26.4 |

INDUSTRIAL APPLICABILITY

According to the above-described embodiments, it is possible to provide a plastic working method and a plastic working apparatus, in which necking or breaking can be suppressed and formability can be improved.

BRIEF DESCRIPTION OF THE REFERENCE SYMBOLS

1: PLASTIC WORKING APPARATUS
3: WORKPIECE (STEEL)
11: MAIN BODY FRAME
12: BOLSTER
13: SLIDE
14: SLIDE DRIVING DEVICE

16: SPACE (SURROUNDING SPACE AROUND STEEL, INTERNAL SPACE OF HOUSING UNIT)
21: MOLDS
31: HEATER FOR SPACE 16 (HEATING UNIT)
32: HEATER FOR MOLDS 21 (HEATING UNIT)
33: HEATING FURNACE FOR WORKPIECE 3 (HEATING UNIT)
41: HEAT INSULATING COVER (INSULATING MEMBER)
51: INERT GAS INTRODUCING UNIT
71: HEATING MEDIUM INTRODUCING UNIT (HEATING UNIT)

The invention claimed is:

1. A plastic working method of steel including austenite, the method comprising:
   physical property analyzing process of measuring $T_\beta$, $\sigma L_\beta$, and $\sigma H_\beta$ for each of strain ratios $\beta$, when $T_\beta$ represents a strain-induced-transformation-maximum-ductility-temperature in the unit of ° C. which is changed depending on the strain ratio $\beta$, $\sigma L_\beta$ represents a standard deviation of a fitted curve of critical equivalent strain which depends on the strain ratio $\beta$ on a lower temperature side than the $T_\beta$, $\sigma H_\beta$ represents a standard deviation of a fitted curve of critical equivalent strain which depends on the strain ratio $\beta$ on a higher temperature side than the $T_\beta$;
   deformation mode analyzing process of analyzing a strain ratio $\beta x$ to be selected from among the strain ratios $\beta$, when the strain ratio $\beta x$ is a strain ratio of an estimated breaking point which is specified during plastic deformation of the steel;
   heating process of heating the steel such that a local temperature $T_{local}$ is within a first temperature range indicated by the following expression 1 after selecting $T_{\beta x}$ from among the $T_\beta$, selecting $\sigma L_{\beta x}$ from among the $\sigma L_\beta$, and selecting $\sigma H_{\beta x}$ from among the $\sigma H_\beta$, when $T_{\beta x}$ represents a strain-induced-transformation-maximum-ductility-temperature in the unit of ° C. for the strain ratio $\beta x$, $\sigma L_{\beta x}$ represents a standard deviation of a fitted curve of critical equivalent strain which depends on the strain ratio $\beta x$ on a lower temperature side than the $T_{\beta x}$, $\sigma H_{\beta x}$ represents a standard deviation of a fitted curve of critical equivalent strain which depends on the strain ratio $\beta x$ on a higher temperature side than the $T_{\beta x}$, and the $T_{local}$ represents a local temperature (° C.) of the estimated breaking point; and
   working process of plastically deforming the steel after the heating:

$$T_{\beta x} - \sigma L_{\beta x} \leq T_{local} \leq T_{\beta x} + 1.25 \times \sigma H_{\beta x} \quad \text{(Expression 1)}.$$

2. The plastic working method according to claim 1, wherein in the deformation mode analyzing process, a change in temperature $\Delta T_{local}$ is further analyzed, when the $\Delta T_{local}$ represents a change in temperature in the unit of ° C. of the local temperature $T_{local}$ which is changed during the plastic deformation of the steel in the working process, and
   wherein in the heating process, heating is performed such that the local temperature $T_{local}$ is within a second temperature range indicated by the following expression 2:

$$T_{\beta x} - \Delta T_{local} - 2 \times \sigma L_{\beta x} \leq T_{local} \leq T_{\beta x} - \Delta T_{local} + 1.25 \times \sigma H_{\beta x} \quad \text{(Expression 2)}.$$

3. The plastic working method according to claim 1, wherein in the heating process, at least one of the steel, a mold, and a surrounding space around the steel is heated such that the local temperature $T_{local}$ is within the first temperature range.

4. The plastic working method according to claim 1, wherein in the heating process, a heating medium is heated such that the local temperature $T_{local}$ is within the first temperature range, and
   wherein in the working process, the steel is plastically deformed using a pressure of the heating medium.

5. The plastic working method according to claim 2, wherein in the physical property analyzing process, the estimated breaking point, the strain ratio $\beta x$, and the change in temperature $\Delta T_{local}$ are analyzed using a plastic working simulation.

6. A plastic working apparatus which performs the plastic working method according to claim 1, the apparatus comprising:
   a housing unit that accommodates the steel and a mold;
   heating units that heat at least two of the steel, the mold, and a surrounding space around the steel;
   a working unit that plastically deforms the steel using the mold; and
   a main body frame,
   wherein the heating units include two or more selected from the group consisting of:
   a heater attached to the main body frame of the housing,
   a heater attached to an inside of the mold, and
   a heating furnace provided outside the plastic working apparatus.

7. The plastic working apparatus according to claim 6, further comprising
   an insulating member that is arranged to cover the housing unit.

8. The plastic working apparatus according to claim 6, further comprising
   a temperature measuring unit that measures respective temperatures of the steel, the mold, and an internal space of the housing unit.

9. A plastic working apparatus which performs the plastic working method according to claim 4, the apparatus comprising:
   a housing unit that accommodates the steel and a mold;
   a heating medium introducing unit that introduces the heating medium into the mold;
   heating units that heat at least two of the steel, the mold, and a surrounding space around the steel and the heating medium;
   a working unit that plastically deforms the steel using a pressure of the heating medium; and
   a main body frame,
   wherein the heating units include two or more selected from the group consisting of:
   a heater attached to the main body frame of the housing,
   a heater attached to an inside of the mold,
   a heating furnace provided outside the plastic working apparatus, and
   a heater configured to heat the heating medium.

10. The plastic working apparatus according to claim 9, further comprising
    an insulating member that is arranged to cover the housing unit.

11. The plastic working apparatus according to claim 9, further comprising
    a temperature measuring unit that measures respective temperatures of the steel, the mold, an internal space of the housing unit, and the heating medium.

* * * * *